United States Patent [19]

Dye

[11] Patent Number: 4,769,047

[45] Date of Patent: Sep. 6, 1988

[54] PROCESS FOR THE PRODUCTION OF ETHYLENE OXIDE

[75] Inventor: Robert F. Dye, Sugarland, Tex.

[73] Assignee: Shell Oil Company, Houston, Tex.

[21] Appl. No.: 67,038

[22] Filed: Jun. 29, 1987

[51] Int. Cl.$^4$ ............................................. B01D 53/04
[52] U.S. Cl. ........................................ 55/26; 55/31; 55/62; 55/63; 55/68; 55/74; 55/75; 585/821; 585/822
[58] Field of Search ............... 55/25, 26, 31, 58, 62, 55/63, 68, 74, 75; 585/820–822

[56] References Cited

U.S. PATENT DOCUMENTS

| | | | |
|---|---|---|---|
| 1,865,422 | 7/1932 | Askenasy | 55/25 |
| 2,823,763 | 2/1958 | Maslan | 55/63 X |
| 3,078,636 | 2/1963 | Milton | 55/63 |
| 3,078,637 | 2/1963 | Milton | 55/68 |
| 3,176,445 | 4/1965 | Collins et al. | 55/58 |
| 3,266,221 | 8/1966 | Avery | 55/58 |
| 3,273,314 | 9/1966 | Quinn | 55/63 |
| 3,331,190 | 7/1967 | Glew et al. | 55/63 |
| 3,867,113 | 2/1975 | Foster et al. | 55/68 X |
| 3,870,482 | 3/1975 | Walker et al. | 55/63 X |
| 3,948,621 | 4/1976 | Cocuzza et al. | 55/30 X |
| 4,106,917 | 8/1978 | Fields et al. | 55/31 |
| 4,263,018 | 4/1981 | McCombs et al. | 55/25 X |
| 4,493,715 | 1/1985 | Hogan et al. | 55/68 |
| 4,498,910 | 2/1985 | Benkmann | 55/26 X |
| 4,696,680 | 9/1987 | Ghate et al. | 55/68 X |

FOREIGN PATENT DOCUMENTS

| | | | |
|---|---|---|---|
| 254430 | 11/1962 | Australia | 55/68 |
| 111911 | 6/1984 | European Pat. Off. | 55/68 |
| 13081 | 4/1973 | Japan | 55/63 |

*Primary Examiner*—Robert Spitzer
*Attorney, Agent, or Firm*—Ronald R. Reper

[57] ABSTRACT

In a process for the direct oxidation of ethylene to ethylene oxide, ethylene is recovered from normally vented gas by contacting first with an activated carbon adsorbent then by pressure swing adsorption with a zeolitic molecular sieve adsorbent.

5 Claims, No Drawings

PROCESS FOR THE PRODUCTION OF ETHYLENE OXIDE

BACKGROUND OF THE INVENTION

The present invention relates to a process for the production of ethylene oxide by direct-oxidation which process is rendered more efficient by purification, recovery and recycle of ethylene which conventionally is purged from the process in order to maintain high conversion selectively to the desired ethylene oxide product.

In the direct-oxidation process high purity ethylene and an oxygen-containing gas, such as air or high purity oxygen, are fed separately into a recycle gas stream serving as feed to one or a plurality of conversion reactors containing a supported silver catalyst. A typical feed stream may contain 20-30 mole % ethylene, 3-8 mole % oxygen, 5-10 % carbon dioxide by-product and the balance a diluent, such as nitrogen. The process involves two primary reactions; the desired partial oxidation conversion of ethylene to ethylene oxide which releases about 1600 BTU per pound of ethylene, and the undesired oxidation of ethylene to carbon dioxide which releases about 21,700 BTU per pound of ethylene. In addition a small amount of the ethylene is converted to higher molecular weight hydrocarbons, mostly C3's such as propylene and cyclopropane and C4's such as butane; under some operating conditions hydrocarbons up to about $C_{10}$ may be formed.

The ethylene feed typically is of 95-98 mole % purity. Its purity is of great importance; impurities can have a drastic effect on the efficiency of the process. For example acetylene, even in trace amounts, is both deleterious and hazardous. Organic sulfur compounds, which may be present in petroleum-derived ethylene can have an irreversible poisoning effect on the catalyst. Less drastic, but significant are higher hydrocarbons such as e.g. propylene and propane. They tend to cause "hot spots" at the catalyst reaction sites and add significantly to the difficulty of proper control of the temperature. Control of heat release which affects the surface temperature of the catalyst is vital to productive operation. Lack of control of the direct-oxidation reaction may be considered the principal factor contributing to impaired catalyst activity, and attendant loss of yield and productivity. The reaction effluent which may contain 1-3 mole % ethylene oxide and 15-25 mole % ethylene is cooled, compressed and the ethylene oxide removed by sorption in a sorbent such as e.g., cold water, sulfuric acid, methanol and the like; the unsorbed gas is returned to the reaction zone as recycle gas.

To prevent the build-up of undesired components in the gas being recycled, it is conventional to vent, i.e. purge a small amount of said recycled gas, however, with attendant loss of valuable ethylene. It is disclosed e.g. in U.S. Pat. No. 3,176,445 that ethylene may be separated from carbon dioxide by contacting the gaseous mixture with a crystalline zeolite molecular sieve material. Procedures for the recovery of ethylene from ethylene oxide reactor off-gas by pressure swing adsorption using crystalline aluminosilicate molecular sieves are known, and disclosed e.g. in U.S. Pat. No. 3,266,221, incorporated by reference. However, application of such procedures to the purged gas also recovers propylene and other higher hydrocarbon gases together with the ethylene, and results in the return of such undesired components to the reaction zone along with separated ethylene.

A process has now been devised to separate and return the ethylene to the process, while still purging at least a majority of the undesired heavier hydrocarbon components.

SUMMARY OF THE INVENTION

The invention provides an improved process for the recovery of ethylene from gases that include carbon dioxide and a $C_3+$ hydrocarbon fraction comprising pressure swing adsorption with a crystalline zeolitic molecular sieve adsorbent and subsequent separation of the ethylene from the carbon dioxide, the improvement comprising first contacting the gases with an activated carbon adsorbent to sorb at least a portion of the $C_3+$ hydrocarbon fraction prior to contact of the gases with said molecular sieve adsorbent.

More particularly the invention provides an improved process for recovering ethylene from an ethylene oxide reactor vent-gas containing ethylene, carbon dioxide and less than about 0.1 mole % of $C_3$ and higher hydrocarbons, which process comprises (a) contacting said reactor vent-gas with activated carbon in a first adsorption zone to sorb at least a majority of the $C_3$ and higher hydrocarbons onto the activated carbon, (b) passing vent-gas having lowered $C_3$ and higher hydrocarbon content as effluent from said first adsorption zone and introducing same to a second adsorption zone having an inlet and an exit end, and comprised of crystalline zeolite molecular sieve bodies having voids between the bodies, (c) contacting said vent-gas product of step (a) at superatmospheric pressure and a temperature of 0°-175° C. with said molecular sieve bodies thereby selectively coadsorbing said ethylene and carbon dioxide in the molecular sieve, and trapping part of said vent-gas product in said voids, (d) discharging from said second adsorption zone effluent gas having lowered content of ethylene and carbon dioxide, (e) establishing in said second adsorption zone at least an ethylene oxide-carbon dioxide coadsorption front at the inlet end and progressively moving such front longitudinally through said molecular sieve zone to a predetermined location intermediate said inlet and exit ends and terminating the introduction of said gas product of step (a) to said second adsorption zone;

(f) removing at least most of the void space gas through the exit end of said second adsorption zone thereby cocurrently depressuring the zone from the first pressure to a second lower pressure which is less than one-half the first pressure, (g) introducing carbon dioxide purge gas to the exit end of said second adsorption zone and flowing said carbon dioxide longitudinally toward the inlet end, thereby displacing the adsorbed ethylene with the carbon dioxide which is adsorbed, to obtain a desorbate comprising ethylene and carbon dioxide, (h) discharging said desorbate from the inlet of said second adsorption zone, (i) separating the ethylene and carbon dioxide in the desorbate and withdrawing the ethylene as product, and (j) partially removing the adsorbed carbon dioxide displacement gas from said second separation zone for subsequent contact with additional first adsorption zone effluent.

DESCRIPTION OF PREFERRED EMBODIMENTS

The vent-gas from the direct oxidation of ethylene to ethylene oxide with an oxygen-containing gas contains air residues and inert diluent gases such as nitrogen, oxygen, argon, methane and ethane, together with ethylene, carbon dioxide and traces of moisture and low molecular weight, typically $C_3$ and $C_4$, up to about $C_{10}$, hydrocarbons. This vent-gas is typically sent to fuel gas or otherwise disposed of, despite its valuable ethylene content of, up to about 20 to 30 percent by volume.

The present invention provides an improved method wherein the ethylene is selectively and efficiently recovered with lower amount of $C_3$ and higher hydrocarbons whereby the recovered ethylene can be recycled to the ethylene oxide reaction while minimizing the disruptive effect of those higher molecular weight hydrocarbons or passed for use in other processes.

The vent-gas from an ethylene oxide reaction is introduced as feed to a first adsorption zone containing activated carbon at superatmospheric pressure and a temperature in the range from about 0°-150° C. and preferably in the range of about 15°-40° C. Suitable pressures are in the range from about 8 to about 20 $Kg/cm^2$, and preferably from about 10 to 15 $Kg/cm^2$. The contacting of the gas containing the $C_3+$ hydrocarbons with the activated carbon may take place by any known gas-solids contacting procedure, e.g. by contacting the gas with a moving or fluidized bed of sorbent particles, however, preferably and most conveniently the $C_3+$ hydrocarbons are removed by passing the gas through a static bed of granular sorbent at weight hourly space velocities from about 0.05 to about 1.00, and preferably from about 0.10 to about 0.85. The contact bed may be in any configuration adapted for the desired flow rate and the $C_3+$ hydrocarbon content of the gas. The sorbent is used in typical fashion. It is preferably used in a packed bed or column. The use of dual columns allow one to be regenerated for sorbing additional $C_3+$ hydrocarbon while the other is sorbing.

The activated carbon sorbents according to this invention are amorphous particulate solids having a surface area in the range from about 800 to about 2,000 square meters per gram, and preferably in the range from about 900 to about 1500 square meters per gram, as determined by the Brunauer, Emmet and Teller method (BET Method).

Since the vent gas does contain oxygen and the sorption process is exothermic, it is preferred not to contact the vent gas with fresh i.e. previously unused activated carbon, but rather to condition, that is, pretreat the activated carbon with a low molecular weight hydrocarbon stream such as methane or ethane to at least partially load the sorbent pores and thereby minimize the sorption exotherm upon contact with the vent gas. Alternatively, for the first contact with the carbon the vent gas may be admixed with e.g. up to about 50 % V methane to minimize the hazard of the initial exotherm. The object of course is to keep the oxygen levels from rising above flammability levels. The capacity of the active carbon to sorb hydrocarbons will vary somewhat depending upon the partial pressure of the hydrocarbon in the vent-gas, but for $C_1$ to $C_4$ hydrocarbons will generally be in the range from about 2 to about 12 pounds of hydrocarbon per 100 pounds of sorbent. Although some ethylene is sorbed onto the carbon and is lost during regeneration, this amount is trivial with respect to the amount that is recovered according to the invention.

Activated carbon sorbent regeneration can be accomplished using hot methane or steam. Hot methane is preferred where the desorbed $C_2+$ hydrocarbons are to be burned as fuel. The heat of desorbing all desorbate molecules will need to be provided. For example, methane preheated to about 200° C. can be brought into the first adsorption zone and exit said zone at a temperature of about 160° C. In order to cool the carbon adsorbent bed, it is advisable to follow the hot methane with ambient temperature methane. This procedure leaves methane sorbed on the carbon bed and tends to minimize exotherms at the start of sorption of additional vent-gas.

In accordance with the invention the vent-gas product from the first adsorption zone is passed to a second adsorption zone where it contacts crystalline zeolitic molecular sieve bodies having voids therebetween. Such molecular sieves are three dimensional crystalline aluminosilicates physically characterized by uniformly sized small pores leading from the exterior surface to an internal three-dimensional cagework formed of interconnected silica and alumina tetrahedra. Only about 1% of the available surface area of these bodies is on the outer side so that most of the adsorption occurs by passage of molecules through the pores into this inner cagework, and adsorption therein. This is in contrast to more conventional adsorbents such as activated carbon and silica gel which do not have large inner adsorption regions and consequently are characterized by lower adsorptive capacity. These crystalline molecular sieves have a particularly strong affinity for molecules which are unsaturated, polar or polarizable, thereby accounting for their selectivity for ethylene, which is an unsaturated molecular, and carbon dioxide which is polar. The molecular sieve adsorbent is typically employed in the form of compressed pellets which may contain a clay binder.

Among the crystalline molecular sieves suitable for use in the process are the naturally occurring chabazite, erionite, mordenite and faujasite. Suitable synthetic molecular sieves include types A, D, L, T, X, and Y. Preferred zeolitic sieves have pore sizes of at least 4.6 Angstrom units, and include calcium-rich chabazite, faujasite and divalent cationic forms of zeolites A, D, and R. The larger pore size enables more rapid adsorption and desorption of the carbon dioxide molecules leading to faster and therefore more efficient operating cycles.

Pressure swing adsorption procedure suitably used in the second adsorption zone are by now well known, and are described e.g. in U.S. Pat. Nos. 3,266,221 and 4,263,018 incorporated by reference, and will be described only briefly. The gas mixture product from the first, activated carbon-containing adsorption zone is introduced as feed to the inlet of the second adsorption zone and contacted with the molecular sieve at a first superatmosphereic pressure and a temperature of 125° to 175° C. The ethylene and carbon dioxide are selectively coadsorbed by the molecular sieve, and part of the gas is trapped in the void space between the sieve bodies. Carbon dioxide and ethylene form a coadsorption composition. In the range from about 20 to 40 mol percent ethylene (60–80 mol percent carbon dioxide), this coadsorbate is more strongly held by the molecular sieve than is the balance of either component which is in excess of the coadsorption composition. The latter is somewhat varible depending upon the conditions of temperature and pressure. For example if ethylene is present in the feed gas mixture in excess over the ethylene-carbon dioxide coadsorption composition, that excess ethylene will pass beyond the coadsorption composition mass transfer zone and form its own adsorption zone farther into the bed. Conversely, if carbon dioxide is in excess, that excess will be adsorbed in the zone beyond the coadsorption composition zone. Accordingly the ethylene is recovered with greater efficiency if it is all contained in the coadsorption zone.

As the flow of feed gas mixture into the molecular sieve bed continues, an ethylene and carbon dioxide-depleted effluent is discharged from the opposite or exit end of the bed. This effluent is primarily the diluent gas such as nitrogen, argon and or methane, and may contain other components of the feed gas mixture which are less strongly held than the ethylene and carbon dioxide. Any water present in the feed gas is retained by the molecular sieve.

The ethylene oxide-carbon dioxide coadsorption front moves longitudinally through said second (molecular sieve) adsorption zone towards the exit end to a predetermined location intermediate the inlet and exit ends, and the feed flow is terminated. The coadsorption front and the ethylene adsorption front (when present) are not permitted to "breakthrough" at the exit end of the zone. The term "breakthrough" herein refers to that point of time in an adsorption step at which the concentration of a selected component materially increases in the effluent. The adsorption step is preferably terminated when the ethylene-carbon dioxide coloaded sieve occupies about 0.8 of the total volume of the bed. The remainder of the bed is used during the first desorption stage.

The adsorption pressure may be any superatmospheric pressure higher than the desorption pressure and the pressures should be in a ratio of about 2 to 1 to obtain reasonable adsorbate working loadings of the process. Temperatures in the range from about 100° C. to about 175° C. may be employed. Temperatures below about 100° C. require undesirably high pressure swing to obtain acceptable working loadings of ethylene. Temperatures above about 175° C. lead to decomposition of the ethylene.

Desorption is performed in three stages. During the first stage at least most of the void space gas is removed through the exit end of the second adsorption zone thereby cocurrently depressuring said zone from the first higher pressure to a second lower pressure which is less than one-half of the first pressure. During this first desorption stage, a portion of the ethylene loaded in the bed during adsorption is displaced toward the exit end by the non-adsorbed gas flow. The portion of the bed which was not used for ethylene adsorption during the adsorption step is now used to readsorb this shifting load. Also as the void gas is drawn off it passes through the unused part of the molecular sieve bed and its ethylene content is adsorbed therein.

During the cocurrent blowdown step the ethylene-carbon dioxide adsorption front moves closer to the exit end and the leading edge may reach this end. At the end of the blowdown the bed contains an essentially uniform loading of coadsorbed ethylene and carbon dioxide of approximately the same ratio as was the loading in equilibrium with the adsorption feed. The blowdown gas is essentially the vent-gas depleted in ethylene and the $C_2{}^+$ hydrocarbons and having reduced carbon dioxide content, and may be discarded.

The second stage of desorption is the passage of carbon dioxide or methane purge gas through the molecular sieve bed in a direction countercurrent to that of the preceding adsorption and depressurization steps. The purge gas e.g., carbon dioxide may be at any desired temperature and pressure, but preferably is at the same temperature as that employed in the adsorption step in order to obtain the benefits of near isothermal operation. During this stage a mass transfer exchange front passes through the bed, the carbon dioxide being adsorbed and in so doing it displaces or desorbs the ethylene from the bed. The carbon dioxide loading behind the exchange front is increased to the loading which is in equilibrium with pure carbon dioxide under the existing conditions of temperature and pressure. The vapor phase carbon dioxide partial pressure at the leading edge of the front is that in equilibrium with the co-adsorbed phase on the bed after current blowdown.

At the end of the second desorption stage the bed is loaded with carbon dioxide, which loading is too high to permit a significant loading of ethylene in the succeeding adsorption step. Accordingly about 85 to 95% by weight of the carbon dioxide is removed from the bed by withdrawing carbon dioxide from one end of the bed thereby reducing the pressure of the gas in equilibrium with the bed. The reactivation pressure needed to reduce the carbon dioxide loading to the desired level at the operating temperature may be determined in a manner well known to those skilled in the adsorption art or from an isotherm chart for the particular molecular sieve in the bed. The reactivation of the carbon dioxide purge-containing sieve zone may be effected by flowing at least part of the ethylene and carbon dioxide-depleted effluent from the adsorption step through the zone.

The desired ethylene is recovered from the second stage desorbate by separation from carbon dioxide, which separation may be accomplished by conventional liquid adsorption methods such as e.g. contact with aqueous monoethanolamine or hot potassium carbonate followed by aqueous ammonia treating and caustic scrubbing. The separated ethylene is compressed and recycled back to the ethylene oxide reaction. The carbon dioxide may be recycled with the carbon dioxide desorbed during the reactivation or third desorption stage as at least part of the purge gas for the second desorption stage following the cocurrent blowdown or depressurization step.

The foregoing description of the pressure swing adsorption process in the second adsorption zone of the instant process has been presented in its simplest form with only one molecular sieve bed consecutively experiencing the adsorption step and three desorption stages. However, most large scale installations require multiple, e.g. three or four or more adsorption beds in the second adsorption zone so that the flows of feed gas and ethylene are continuous.

What is claimed is:

1. In a process for the recovery of ethylene from gases that include carbon dioxide and a $C_3{}^+$ hydrocarbon fraction comprising pressure swing adsorption with a crystalline zeolitic molecular sieve adsorbent and subsequent separation of the ethylene from the carbon dioxide, the improvement comprising first contacting the gases with an activated carbon adsorbent to sorb at least a portion of the $C_3{}^+$ hydrocarbon fraction prior to contact of the gases with said molecular sieve adsorbent.

2. An improved process for recovering ethylene from an ethylene oxide reaction vent-gas containing ethylene, carbon dioxide and less than about 0.1 mole % of $C_3$ and higher hydrocarbons, which process comprises
- (a) contacting said reaction vent-gas with activated carbon having a surface area in the range of from about 800 to 2,000 square meters per gram, at a temperature in the range from about 0°–150° C., a pressure in the range from about 3 to about 20 kg/cm$^2$ and a weight hourly space velocity from about 0.05 to about 1.00, in a first adsorption zone to sorb a majority of the $C_3$ and higher hydrocarbons in the activated carbon;
- (b) passing vent-gas having lowered $C_3$ and higher hydrocarbon content as effluent from said first adsorption zone and introducing same to a second adsorption zone having an inlet and an exit end, and comprised of crystalline zeolitic molecular sieve bodies having voids between the bodies;
- (c) contacting said vent-gas product of step (a) at superatmospheric pressure and a temperature of 0°–175° C. with said molecular sieve bodies thereby selectively co-adsorbing said ethylene and crbon dioxide in the molecular sieve, and trapping part of said vent-gas product in said voids;
- (d) discharging from said second adsorption zone effluent gas having lowered content of ethylene and carbon dioxide,
- (e) establishing in said second adsorption zone at least an ethylene oxide-carbon dioxide co-adsorption front at the inlet end and progressively moving such front longitudinally through said molecular sieve zone to a predetermined location intermediate said inlet and exit ends and terminating the introduction of said gas product of step (a) to said second adsorption zone;
- (f) removing at least most of the void space gas through the exit end of said second adsorption zone thereby co-currently depressuring the zone from the first pressure to a second lower pressure which is less than one-half the first pressure,
- (g) introducing carbon dioxide purge gas to the exit end of said second adsorption zone and flowing said carbon dioxide longitudinally toward the inlet end, thereby displacing the adsorbed ethylene with the carbon dioxide which is adsorbed, to obtain a desorbate comprising ethylene and carbon dioxide,
- (h) discharging said desorbate from the inlet of said second adsorption zone,
- (i) separating the ethylene and carbon dioxide in the desorbate and withdrawing the ethylene as product, and
- (j) partially removing the adsorbed carbon dioxide displacement gas from said second separation zone for subsequent contact with additional first adsorption zone effluent.

3. A process as in claim 2 wherein the first adsorption zone intermittently is reactivated by introducing methane purge gas through said zone thereby displacing the adsorbed $C_3$ and heavier hydrocarbons with methane which is sorbed onto the activated carbon, and withdrawing a first adsorption zone desorbate.

4. A process as in claim 2 wherein the vent-gas feed mixture to the first adsorption zone contacts the activated carbon at a temperature in the range from about 15° to about 40° C. and a pressure in the range from about 8 to about 20 Kg/cm$^2$.

5. A process as in claim 2 wherein said first adsorption zone comprises a pair of beds operatively connected to enable one bed to be regenerated while the other is sorbing $C_3{}^+$ hydrocarbons.

* * * * *